US007235687B2

(12) United States Patent
Fournie-Zaluski et al.

(10) Patent No.: US 7,235,687 B2
(45) Date of Patent: Jun. 26, 2007

(54) DERIVATIVES OF 4,4'-DITHIOBIS-(3-AMINOBUTANE-1-SULFPHONATES) AND COMPOSITIONS CONTAINING SAME

(75) Inventors: Marie-Claude Fournie-Zaluski, Paris (FR); Catherine Llorens-Cortes, Bures sur Yvette (FR); Bernard Pierre Roques, Paris (FR); Pierre Corvol, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 10/521,171

(22) PCT Filed: Jul. 16, 2003

(86) PCT No.: PCT/FR03/02242

§ 371 (c)(1),
(2), (4) Date: Sep. 21, 2005

(87) PCT Pub. No.: WO2004/007441

PCT Pub. Date: Jan. 22, 2004

(65) Prior Publication Data

US 2006/0135602 A1 Jun. 22, 2006

(30) Foreign Application Priority Data

Jul. 16, 2002 (FR) .................................. 02 08977
Mar. 20, 2003 (FR) .................................. 03 03425

(51) Int. Cl.
*C07C 309/00* (2006.01)
*A61K 31/255* (2006.01)
*A61K 31/185* (2006.01)

(52) U.S. Cl. ........................ 562/101; 514/517; 514/553
(58) Field of Classification Search ..................... None
See application file for complete search history.

(56) References Cited

FOREIGN PATENT DOCUMENTS

WO      WO 99/36066 A1      7/1999

OTHER PUBLICATIONS

Chauvel, et al, "Investigation of the active site of aminopeptidase a using a series of new thiol-containing inhibitos". J. Med. Chem. (1994). 37(9):1339-1346.
Chavel, et al, "Differential inhibition of aminopeptidase A and aminopeptidase N by New β-amino thiols". J. Med. Chem. (1994). 37(18):2950-2957.
Database Caplus. Database accession No. 1998:505738; Martin, et al, "β-amino-thiols inhibit the zinc metallopeptidase activity of tetanus toxin light chain". American Chemical Society. (1998) RN 213488-11-0.
Martin, et al, "β-amino-thiols inhibit the zinc metallopeptidase activity of tetanus toxin light chain". J. Med. Chem. (1998). 41(18):3450-3460.

*Primary Examiner*—Sikarl A. Witherspoon
(74) *Attorney, Agent, or Firm*—Browdy and Neimark, PLLC

(57) ABSTRACT

The invention relates to the bis-hydrochloride of 4,4'-dithio-bis-(3-aminobutane-1-sodium sulphonate) and the bis-trifluoracetate of 4,4'-dithiobis-(3-aminobutane-1-sulphonate of 2,2-dimethylpropyl). The invention also relates to a pharmaceutical composition comprising one of said compounds and to the use of one of said compounds for the production of a medicament. The invention is suitable for use in a treatment method for hypertension and indirectly- or directly-linked illnesses.

7 Claims, 1 Drawing Sheet

DERIVATIVES OF 4,4'-DITHIOBIS-(3-AMINOBUTANE-1-SULFPHONATES) AND COMPOSITIONS CONTAINING SAME

BACKGROUND OF THE INVENTION

The present invention relates to novel compounds, to methods for preparing the compounds, pharmaceutical formulations comprising these compounds, and the use of these compounds in therapy. In particular, the present invention relates to compounds that are useful in the treatment and prevention of primary and secondary arterial hypertension, ictus, myocardial ischaemia, cardiac and renal insufficiency, myocardial infarction, peripheral vascular disease, diabetic proteinuria, Syndrome X and glaucoma.

Arterial hypertension is a disorder whose causes generally remain unknown. Extrinsic factors which may participate include obesity, sedentary lifestyle, excessive alcohol or salt intake, and stress. Intrinsic factors suggested to play a role include fluid retention, sympathetic nervous system activity and constriction of blood vessels. Arterial hypertension can contribute directly or indirectly to diseases of the heart, the peripheral and cerebral vascular system, the brain, the eye and the kidney.

Treatment of arterial hypertension includes the use of diuretic agents, adrenergic blockers, inhibitors of angiotensin converting enzyme, angiotensin receptor antagonists, calcium antagonists and direct vasodilators. It is desirable to identify further compounds to treat arterial hypertension.

BRIEF DESCRIPTION OF THE INVENTION

The present inventors have identified novel compounds which are effective in reducing arterial hypertension and thus have utility in treating arterial hypertension and the diseases to which it indirectly and directly contributes.

Accordingly the invention provides the following compounds:
- 4,4' dithiobis (sodium 3-aminobutane-1-sulfonic acid);
- 4,4' dithiobis (2,2dimethypropyl)-3-aminobutane-1-sulfonate.

In another aspect, the present invention discloses a method for prevention or treatment of arterial hypertension and indirectly and directly related diseases, comprising administration of a therapeutically effective amount of a compound of this invention. In another aspect, the present invention provides pharmaceutical compositions comprising one or more compounds of the invention, preferably in association with a pharmaceutically acceptable diluent or carrier.

In another aspect, the present invention provides one or more compounds of the invention for use in therapy, and in particular, in human medicine.

In another aspect, the present invention provides the use of one or more compounds of the invention for the manufacture of a medicament for the treatment of arterial hypertension and indirectly and directly related diseases.

In another aspect, the present invention provides a method of treatment of a patient suffering from arterial hypertension and indirectly and directly related diseases comprising the administration of a therapeutically effective amount of one or more compounds of the invention.

DETAILED DESCRIPTION OF THE INVENTION

Figure 1:
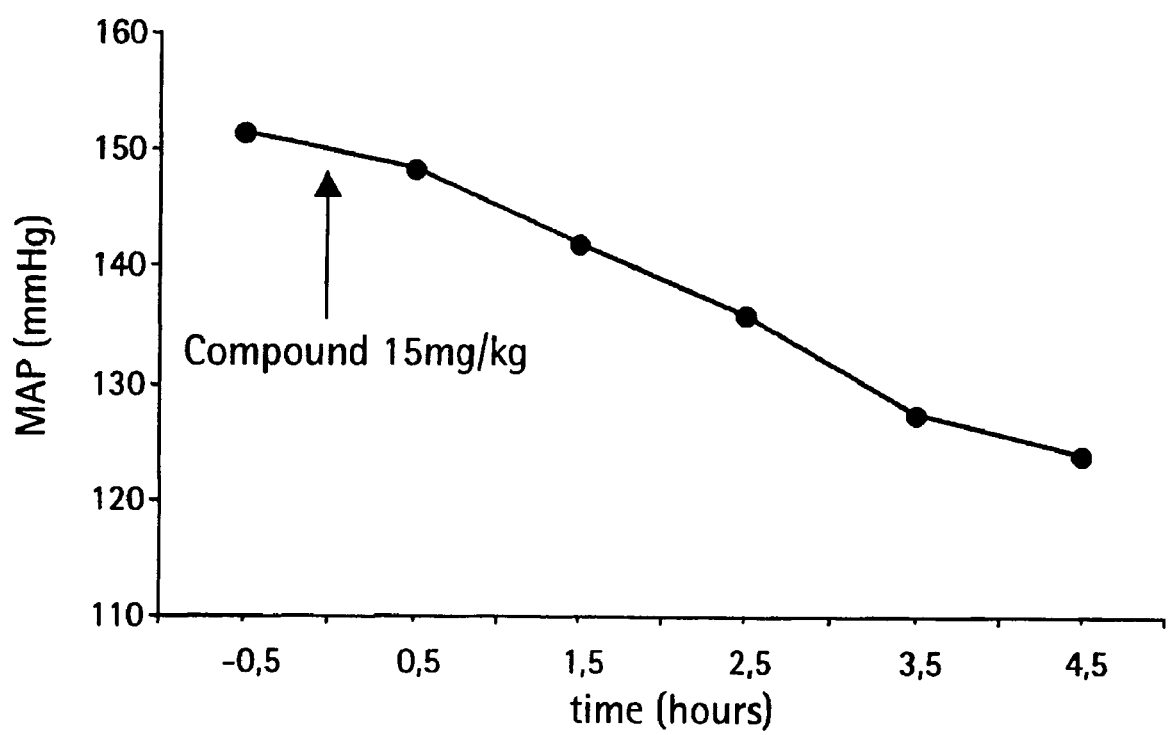
FIG. 1 demonstrates the effect of the compound of Example 1 on blood pressure in hypertensive rats.

The present invention provides methods of prevention or treatment of arterial hypertension and diseases to which arterial hypertension directly or indirectly contributes. Such diseases include diseases of the heart, the peripheral and cerebral vascular system, the brain, the eye and the kidney. In particular diseases include primary and secondary arterial hypertension, ictus, myocardial ischaemia, cardiac and renal insufficiency, myocardial infarction, peripheral vascular disease, diabetic proteinuria, Syndrome X and glaucoma.

As used herein, "a compound of the invention" means a compound described above or pharmaceutically acceptable salts or solvate thereof.

The person skilled in the art will recognize that stereocenters exist in the compounds of the invention. Accordingly, the present invention includes all possible stereoisomers and geometric isomers of the compounds of formula (I) and includes not only racemic compounds but also the optically active isomers as well. When a compound of formula (I) is desired as a single enantiomer, it may be obtained either by resolution of the final product or by stereospecific synthesis from either isomerically pure starting material or any suitable intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds The specialist in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) are within the scope of the present invention.

It will also be appreciated by the specialist in organic chemistry that many organic compounds can exist in more than one crystalline form. For example, crystalline form may vary from solvate to solvate. Thus, all crystalline forms of the compounds of the invention or the pharmaceutically acceptable solvates thereof are within the scope of the present invention.

It will also be appreciated by the person skilled in the art that as well as being used in the parent compound form the compounds of the present invention may also be utilized in the form of pharmaceutically acceptable salts or solvates thereof. The pharmaceutically acceptable salts of the compounds of the invention include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic etc. Other acids such as oxalic, while not in themselves pharmaceutically acceptable, may be useful in the preparation of salts useful as intermediates in obtaining the compounds of the present invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts and solvates.

For example, preferred salt forms include:

4,4' dithiobis (sodium 3-aminobutane-1-sulfonate) bis chlorohydrate;

4,4' dithiobis (2,2dimethypropyl)-3-aminobutane-1-sulfonate), bis trifluoroacetate.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients. The carrier(s) must be "acceptable" in the sense of being compatible with the other ingredients of the formulation and not deleterious to the subject receiving them.

While it is possible that compounds of the present invention may be therapeutically administered as the raw chemical, it is preferable to present the active ingredient as a pharmaceutical formulation.

Accordingly, the present invention further provides for a pharmaceutical formulation comprising a compound of the present invention or a pharmaceutically acceptable salt or solvate thereof in association with one or more pharmaceutically acceptable carriers and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation, although the most suitable route may depend upon for example the condition and disorder of the recipient. The formulations may conveniently be presented in unit dosage form and may be prepared by any of the methods well known in the art of pharmacy. All methods include the step of associating the compounds ("active ingredients") with the carrier which constitutes one or more accessory ingredients. In general the formulations are prepared by uniformly and intimately associating the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, gum arabic, gelatin, sorbitol, tragacanth, mucilage of starch, polyvinylpyrrolidone or hydroxymethyl cellulose), fillers (for example, lactose, sucrose, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, and such as syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or gum arabic; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. These preparations may also be formulated as suppositories, e.g., containing conventional suppository excipients such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured excipient such as sucrose and gum arabic or tragacanth, and pastilles comprising the active ingredient in an excipient such as gelatin and glycerin or sucrose and gum arabic.

For topical administration to the epidermis, the compounds may be formulated as creams, gels, ointments or lotions or as a transdermal patch.

The compounds may also be formulated as depot preparations. These long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For intranasal administration the compounds of the present invention may be used, for example as a liquid spray, as a powder or in the form of drops.

For administration by inhalation the compounds according to the present invention are conveniently delivered in the form of an aerosol spray presentation from a pressurised container or a nebuliser, with the use of a suitable propellant, e.g. 1,1,1,2-trifluoroethane (HFA 134A) and 1,1,1,2,3,3, -heptafluoropropane (HFA 227), carbon dioxide or other suitable gas. In the case of a pressurised aerosol the exact dosage may be determined by providing a valve adapted to deliver a metered amount. Capsules and cartridges of e.g. gelatin for use in an inhaler or insufflator may be formulated so as to contain a powder mix of a compound of the present invention and a suitable powder excipient such as lactose or starch.

In addition to the ingredients particularly mentioned above, the formulations may include other agents conventional in the art having regard to the type of formulation in question, for example those suitable for oral administration may include flavouring agents.

It will be appreciated by the person skilled in the art that reference herein to treatment extends to prophylaxis as well as the treatment of established diseases or symptoms. Moreover, it will be appreciated that the amount of a compound of the present invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the present invention may contain between 0.1–99% of the active ingredient, conveniently from 30–95% for tablets and capsules and 3–50% for liquid preparations.

The compound of the present invention for use in the present invention may be used in association with one or more other therapeutic agents for example, beta-adrenergic receptor antagonists, calcium channel blocking agents, thiazide diuretics, angiotensin receptor antagonists and angiotensin converting enzyme inhibitors. The present invention thus provides in a further aspect the use of a combination comprising a compound of formula (I) with a further therapeutic agent in the treatment of arterial hypertension.

When the compounds of the present invention are used in association with other therapeutic agents, the compounds may be administered either sequentially or simultaneously by any suitable route.

The associations referred to above may suitably be presented for use in the form of a pharmaceutical formulation and thus pharmaceutical formulations comprising a association as defined above optimally together with a pharmaceutically acceptable carrier or excipient comprise a further aspect of the present invention. The individual components of such associations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any suitable formulation, suitably in a manner known for such compounds in the art.

When a compound of the present invention is used in association with a second therapeutic agent active against the same disease, the dose of each compound may differ from that administered when the compound is used alone. Appropriate doses will be readily determined by the person skilled in the art.

The compounds of the present invention may be prepared by way of the following Examples which should not be construed as constituting a limitation thereto.

EXAMPLE 1

4,4' dithiobis (sodium 3-aminobutane-1-sulfonate) bis chlorhydrate

Step 1: Synthesis of the Chlorhydrate of 2-amino-4-chloro-1-ethoxycarbonyl propane

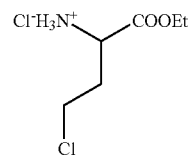

A solution of 20 g L-homoserine in 50 mL of absolute ethanol was cooled to 0° C. and 121 mL (10 eq) SOCl$_2$ was added dropwise. The mixture was warmed to room temperature and then heated at reflux for 8 h. The solution was evaporated in vacuo and the residue was treated with Et$_2$O. The precipitate was filtered and washed three times with Et$_2$O. White solid: 31.2 g (92%). Rf (CH$_2$Cl$_2$/MeOH/AcOH: 7/3/0.5) 0.59.

Step 2: Synthesis of Ethyl 2-t-butoxycarbonylamino-4-chlorobutanoate.

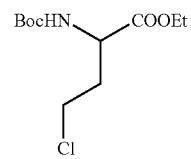

The preceding compound (31.2 g), dissolved in 80 ml DMF was cooled to −10° C., then a solution of (Boc)$_2$O (37.1 g) in 80 mL DMF and 23.8 ml Et$_3$N was added. The mixture was stirred at room temperature overnight. The solution was evaporated in vacuo and the residue partitioned between H$_2$O and Et$_2$O. The organic layer was washed, dried over Na$_2$SO$_4$, filtered and evaporated in vacuo. Beige solid, 40.7 g (99%). Rf (EtOAc/nHex: 3/1) 0.66.

Step 3: Synthesis of Sodium, 3-tert-butoxycarbonylamino-3-ethoxycarbonyl-propane-1 sulfonate

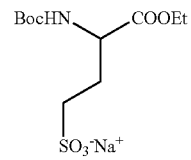

The preceding compound (10.8 g) was dissolved in a mixture of 150 ml dioxane/150 ml H$_2$O and 6.1 g NaI and 25.6 g Na$_2$SO$_3$ were added. The mixture was heated at reflux for 15 hours, then, evaporated in vacuo. The residue was dissolved in EtOH (250 ml). The precipitate was eliminated and the filtrate was evaporated in vacuo. A white powder was obtained; 12 g (89%). Rf (CH$_2$Cl$_2$/MeOH: 8/2) 0.18.

Step 4: Synthesis of Sodium 3-tert-butoxycarbonylamino-4-hydroxy-butane-1-sulfonate

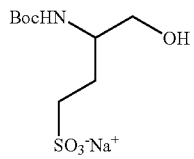

The preceding ester (10 g) was dissolved in 125 ml absolute EtOH and 125 ml anhydrous THF, then 5.1 g of anhydrous LiCl and 4.9 g NaBH$_4$ were added. The mixture was stirred for 17 h at room temperature. Acetic acid (60 ml) was added at 0° C. and the mixture was evaporated in vacuo. The crude product was purified by chromatography on silica gel using EtOAc/MeOH: 8/2 as eluent: White solid, 7.16 g (82%). Rf (EtOAc/MeOH: 7/3) 0.32.

Step 5: Synthesis of Sodium 4-acetylsulfanyl-3-tert-butoxy-carbonylamino-butane-1-sulfonate.

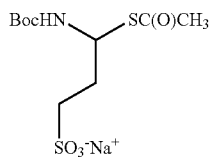

A solution of 13 g triphenylphosphine in anhydrous THF (170 ml) was cooled at 0° C. and 10 ml of diisopropyla-zodicarboxylate were added. The solution was stirred for 45 min at the same temperature. A solution of the preceding alcohol (7 g) in THF (125 ml)+DMF (40 ml) was added, followed 15 min later by 4 ml CH$_3$COSH and the mixture was stirred overnight at room temperature. After evaporation in vacuo, the residue was dissolved in EtOAc and washed with NaHCO$_3$ (10%), H$_2$O, brine and dried over Na$_2$SO$_4$. After evaporation, n.Hex/EtOAc was added and the precipitate eliminated. The filtrate was evaporated and the residue purified by chromatography on silica gel using nHex/EtOAc: 4/1 as eluent. Oily product 8.4 g (80%) Rf(CH$_2$Cl$_2$//MeOH: 8/2) 0.20.

Step 6: Synthesis of 4,4' dithiobis (sodium3-aminobutane-1-sulfonate) bis chlorhydrate.

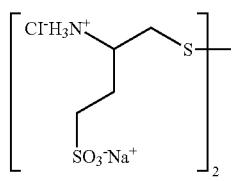

350 mg of the preceding compound were heated at reflux with 15 ml HCl 6N for 3 h. The solution was evaporated in vacuo and the residue dissolved in EtOH/H$_2$O: 1/4 and treated with a solution of iodine until a persistent yellow color was observed. The solution was evaporated and the final compound precipitated with Et$_2$O. White solid highly hygroscopic 200 mg (80%).

Alternatively the parent compound can be prepared from the free thiol as follows:

7.0 g of EC33 are dissolved in 100 ml of methanol with stirring. A solution of 7.32 g iodine in 100 ml of methanol is added dropwise until decolouration ceases. The resulting precipitate is filtered and washed with 20 ml volumes of methanol until the liquid from washing is colourless. The precipitate is washed with ether and dried under reduced pressure to give 4.1 g of a white solid.

$[\alpha]_D^{20}$=+194.5 water, c=1.33;

Calculated % C 26.07, H 5.47, N 7.60, O 26.05, S 34.81
Found % C 25.61, H 5.60, N 7.39, O 25.99, S 33.50;
NMR (D$_2$O, 400 MHz): δ 2.1 (m, 2H, CH$_2$β); 2.85 (dd, 1H, CH$_2$γ); 2.95 (t, 2H, CH$_2$β'); 3.10 (dd, 1H, CH$_2$γ); 3.70 (m, 1H, CH α).

Rf=0.26 in isopropanol/water/acetic acid: 8/2/1, v/v/v

EXAMPLE 2

4,4' dithiobis (2,2dimethypropyl)-3-aminobutane-1-sulfonate), bis trifluoroacetate Step 1: Benzyloxycarbonyl-L-homocystine

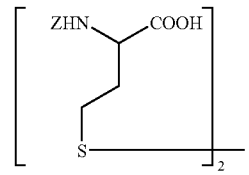

L-homocystine (5 g) was dissolved in a mixture (80 ml) of dioxane/H$_2$O. At 0° C. and under stirring, 1.52 g (2.1 eq) of NaOH and a solution of 7.8 g (2.4 eq) of benzylchloroformate in 40 ml dioxane were added. The pH was maintained at 9 by addition of a solution of NaOH 1M. After stirring for 2.30 h at room temperature, 100 ml H$_2$O were added and the white precipitate was extracted by Et20 (2×50 ml). The aqueous phase was acidified to pH 1 and the precipitate was extracted by EtOAc (4×80 ml). The organic phase was washed, dried over Na$_2$SO$_4$, filtered and evaporated in vacuo. White solid 10.2 g (100%).

Step 2: Ethyl benzyloxycarbonyl-L-homocystinate.

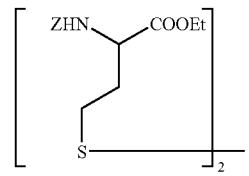

Z-L-homocystine (10 g) was dissolved in 150 ml absolute EtOH. A solution of 1 ml SOCl$_2$ in CH$_2$Cl$_2$ (17 ml) was added at 0° C. and the mixture was heated under reflux for 4 h. The mixture was evaporated in vacuo and the residue dissolved in CH$_2$Cl$_2$. The organic phase was washed, dried over Na$_2$SO$_4$, filtered and evaporated in vacuo. Yellow paste, 9 g (80%) Rf (EtOAc/cHex=1/1) 0.59

Step 3: Ethyl-2-benzyloxycarbonylamino-4-(2,2-dimethypropyl)-1-sulfonyl butanoate.

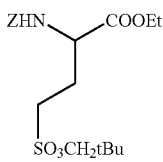

The preceding compound (9 g) was dissolved in a mixture CCl$_4$/EtOH and Cl$_2$ gas was bubbled through the mixture for 45 min. After evaporation in vacuo, a yellow paste was obtained which was dissolved in 200 ml CH$_2$Cl$_2$. Then, 3.48 g neopentyl alcohol and 5.85 ml Et$_3$N were added. The mixture was stirred overnight, evaporated in vacuo and purified by chromatography on silica gel, using EtOAc/cHex: 1/4 as eluent. 11.2 g of a white solid was obtained (90%). Rf (EtOAc/cHex: 1/4) 0.16.

Step 4: Ethyl-2-tert-butoxycarbonylamino-4-(2,2-dimethypropyl)-1-sulfonyl butanoate.

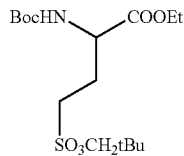

The preceding compound (5.2 g) was dissolved in 30 ml EtOAc and a solution of 4.07 g of Boc$_2$O in 30 ml EtOAc and 400 mg of Pd/C 10% catalyst were added. The mixture was stirred under 250 kPa H$_2$ at 40° C. for 48 h. The mixture was filtered on Celite and the organic phase was evaporated in vacuo (100%) Rf (EtOAc/cHex: 1/4) 0.79.

Step 5: (2,2-dimethypropyl)-3-tert-butoxycarbonylamino-4-hydroxy-butane-1-sulfonate.

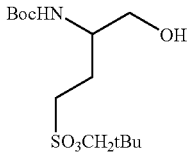

The preceding compound (2.44 g) was dissolved in 120 ml of 50/50 THF/EtOH. The solution was cooled to −10° C. under inert atmosphere and 1.09 g (4 eq) of LiCl and 0.97 g (4 eq) of NaBH$_4$ were added. After 15 min at −10° C., the mixture was stirred at room temperature for 60 h. Then 20 ml of AcOH were added and the mixture was evaporated in vacuo. The residue was dissolved in 400 ml EtOAc, washed with water, brine, and dried over Na$_2$SO$_4$. The crude product was purified by chromatography on silica gel using EtOAc/MeOH/cHex: 1/1/4 as eluent (Rf 0.20) 2.1 g (99%).

Step 6: (2,2-dimethypropyl)-3-tert-butyloxycarbonylamino-4-acetylsulfanyl-butane-1-sulfonate.

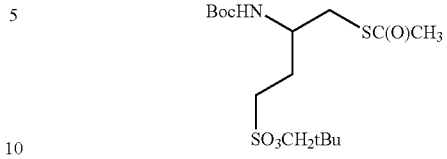

The preceding compound (0.965 g) in 10 ml CHCl$_3$ was cooled to −10° C. and 1.07 ml Et$_3$N and 0.44 ml CH$_3$SO$_2$Cl in 4 ml CHCl$_3$ were successively added. The mixture was stirred at room temperature for 1.5 h. Then 40 ml CHCl$_3$ were added and the organic phase was washed at 0° C. with a solution of NaHCO$_3$ 10%, H$_2$O, HCl 1 N, H$_2$O, brine and dried over Na$_2$SO$_4$. After filtration and evaporation, the crude product (Rf (EtOAc/AcOH/cHex: 1/1/4)=0.41) was dissolved in 15 ml DMF and at −10° C., 0.65 g CH$_3$COSK was added. The mixture was stirred for two days at room temperature. The solvent was evaporated in vacuo and an orange residue was obtained.

Chromatography on silica gel; eluent EtOAc/cHex: 1/4 (Rf=0.15); white solid 0.64 g (57%).

Step 7: 4,4' dithiobis ((2,2-dimethypropyl)-3-tert-butyloxycarbonylamino-butane-1-sulfonate).

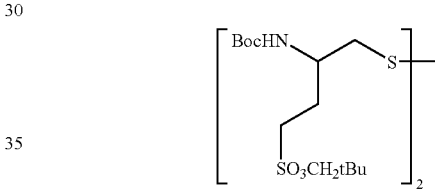

The preceding compound (0.25 g) was dissolved in EtOH/THF: 2/1. Then 60 mg NaOH, dissolved in 1 ml H$_2$O were added. The mixture was stirred under O$_2$ bubbling for 12 h. After evaporation in vacuo, the residue was dissolved in 40 ml H$_2$O/40 ml EtOAc and was acidified to pH 1. The organic layer was isolated, washed, dried over Na$_2$SO$_4$, filtered and evaporated in vacuo. White solid: 0.178 g (80%). Rf (EtOAc/MeOH/cHex: 1/1/4) 0.28.

Step 8: 4,4' dithiobis ((2,2-dimethypropyl)-3-aminobutane-1-sulfonate), bis trifluoroacetate.

The preceding disulfide (0.17 g) was dissolved in 6 ml CH$_2$Cl$_2$ and 6 ml CF$_3$CO$_2$H were added. The mixture was stirred at room temperature for 2 h and evaporated in vacuo. The residue was washed with Et$_2$O. White solid 0.17 g (100%) Rf(CH$_2$Cl$_2$/MeOH: 7/3) 0.47.

$[\alpha]_D^{19}$=+24.8, c=0.995 in EtOH 95%

NMR $^1$H (DMSO): δ 0.90 (s, 9H, tBu); 2.1 (m, 2H, CH$_2$β); 2.70–2.75 (m, 1H, CH$_2$β'); 2.80–2.90 (dd, 1H, CH$_2$β'); 3.00–3.10 (dd, 1H, CH$_2$α); 3.50 (m, 3H, CH α and CH$_2$γ); 3.90 (s, 2H, CH$_2$γ'), 8.1 (s, 2H, NH$_3^+$)

This compound can be converted to the parent molecule or other suitable salts by methods known in the art. For example, to convert to the parent molecule 40 mg of RB 151 are dissolved in 2 ml water. 5 ml of ether are added and then, dropwise, 0.12 ml of aqueous sodium hydroxide solution (1M). The aqueous phase becomes milky and then clarifies rapidly. The mixture is stirred for 30 minutes and the organic phase is separated. The aqueous phase is washed three times with 5 ml of ether. The combined organic phases are dried over sodium sulphate then concentrated under vacuum to give an amorphous powder with a 98% yield.

$[\alpha]_D^{19}=+42.3$ c=0.992 in EtOH 95%

NMR $^1$H (DMSO): δ 0.90 (s, 9H, tBu); 1.65–1.75 (m, 1H, CH$_2$β; 1.90–2.00 (m, 1H, CH$_2$β); 2.70–2.75 (m, 1H, CH$_2$β'); 2.80–2.90 (m, 1H, CH$_2$β'); 3.00–3.10 (m, 1H, CH$_2$α); 3.35–3.50 (m, 2H, CH$_2$γ); 3.80 (s, 2H, CH$_2$γ')

EXAMPLE OF BIOLOGICAL ACTIVITY

Effect on Blood Pressure in Rats

Deoxycorticosterone acetate (DOCA)-salt hypertensive rats were obtained according to Pham, I. et al (1993) J. Pharmacol. Exp. Ther. 265, 1339–1347 with the following modifications: under pentobarbital anaesthesia, unilateral nephrectomy was performed in male Wistar Kyoto rats (300 g) and a pellet of 50 mg of DOCA was implanted s.c. After surgery, the rats were fed on standard rat chow and the drinking water was supplemented with 0.9% NaCl and 0.2% KCl. Hypertension developed 3 weeks after surgery.

To record arterial blood pressure, DOCA-salt rats were anaesthetized with pentobarbital sodium (50 mg/kg i.p., Sentravet laboratory, Plancoët, France), a femoral artery catheter (PE$_{50}$) filled with heparinized saline (250 U/ml) was inserted, then brought under the skin and emerged at the nape of the neck. A flexible metal spring was attached to the skull and neck of the rat and connected to dual channel swivels mounted directly above the cage. This arrangement allowed the rat free movement inside the cage. Each rat was then given an intramuscular injection of 0.1 ml of penicillin-streptomycin (50 000 UI/ml, Boehringer Mannheim, GmbH-Germany) and allowed to recover for at least 24 h prior to the experiment. Mean arterial BP was continuously recorded throughout each experiment using a COBE CDX III pressure transducer (Phymep, Paris, France) connected to the MacLab system (Phymep, Paris, France) composed of a MacLab technology unit and Chart software running on a Macintosh computer.

The compound of Example 1 was administered to the rats by oral gavage in water at 15 mg/kg. As shown in FIG. 1 mean arterial blood pressure was decreased by 3680 Pa, 4.5 hours after administration.

The application of which this description and the claims are a part may be used as basis for priority with respect to any later application. The claims of such a later application may be directed to any new feature or association of new features described in the present document. Its claims may be in the form of product, composition, process or use claims and may comprise, by way of non-limiting example, one or more of the following claims.

The invention claimed is:

1. A compound selected from the group consisting of: 4,4'-dithiobis(sodium 3-aminobutane-1-sulfonic acid), pharmaceutically acceptable salts and solvates thereof; 4,4'-dithiobis(2,2 dimethylpropyl)-3-aminobutane-1-sulfonate, and pharmaceutically acceptable salts and solvates thereof.

2. A compound according to claim 1, formulated for use in therapy.

3. A pharmaceutical composition, characterized in that it comprises a compound according to claim 1, and a pharmaceutically acceptable diluent or carrier.

4. A compound according to claim 1, which is
   - -4,4'-dithiobis(sodium 3-aminobutane-1-sulfonate)bis chlorohyrate; or
   - -4,4'-dithiobis(2,2 dimethylpropyl)-3-aminobutane-1-sulfonate)bis trifluoroacetate.

5. A pharmaceutical composition, characterized in that it comprises a compound according to claim 4, and a pharmaceutically acceptable diluent or carrier.

6. A method of treating arterial hypertension and directly or indirectly related disease, which comprises administering to a patient in need thereof an effective amount of a compound according to claim 1.

7. A method of treating arterial hypertension and directly or indirectly related disease, which comprises administering to a patient in need thereof an effective amount of a compound according to claim 4.

* * * * *